United States Patent
Barral et al.

(10) Patent No.: US 11,026,754 B2
(45) Date of Patent: *Jun. 8, 2021

(54) MOTION EXECUTION OF A ROBOTIC SYSTEM

(71) Applicant: Verily Life Sciences LLC, South San Francisco, CA (US)

(72) Inventors: Joëlle K. Barral, Mountain View, CA (US); Blake Hannaford, Seattle, WA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/878,411

(22) Filed: May 19, 2020

(65) Prior Publication Data

US 2020/0275978 A1    Sep. 3, 2020

Related U.S. Application Data

(63) Continuation of application No. 15/675,029, filed on Aug. 11, 2017, now Pat. No. 10,695,134.

(Continued)

(51) Int. Cl.
*A61B 34/00* (2016.01)
*A61B 34/20* (2016.01)
(Continued)

(52) U.S. Cl.
CPC .............. *A61B 34/20* (2016.02); *A61B 34/30* (2016.02); *A61B 34/35* (2016.02); *A61B 34/37* (2016.02);
(Continued)

(58) Field of Classification Search
CPC ......... A61B 34/20; A61B 34/74; A61B 34/35; A61B 34/37; A61B 34/30;
(Continued)

(56) References Cited

U.S. PATENT DOCUMENTS

| | | |
|---|---|---|
| 6,109,270 A | 8/2000 | Mah et al. |
| 6,723,106 B1 | 4/2004 | Charles et al. |

(Continued)

FOREIGN PATENT DOCUMENTS

| | | |
|---|---|---|
| JP | 2010-524634 A | 7/2010 |
| WO | 98/33451 A1 | 8/1998 |

OTHER PUBLICATIONS

First Chinese Office Action, dated Nov. 4, 2020, issued in corresponding Chinese Application No. 201780051280.0, filed Aug. 22, 2017, 16 pages.

(Continued)

*Primary Examiner* — Ian Jen
(74) *Attorney, Agent, or Firm* — Christensen O'Connor Johnson Kindness PLLC

(57) ABSTRACT

A method of surgical robot operation includes moving a surgical instrument through a medium using the surgical robot, where the surgical robot attempts to move the surgical instrument to a desired position. The method further includes measuring an actual position of the surgical instrument, and calculating a difference between the actual position and the desired position. The actual position of the surgical instrument is adjusted to the desired position using the surgical robot.

20 Claims, 5 Drawing Sheets

Related U.S. Application Data

(60) Provisional application No. 62/379,445, filed on Aug. 25, 2016.

(51) Int. Cl.
    *A61B 34/30*     (2016.01)
    *A61B 34/35*     (2016.01)
    *A61B 34/37*     (2016.01)
    *B25J 9/16*     (2006.01)
    *A61B 90/00*     (2016.01)

(52) U.S. Cl.
CPC .............. *A61B 34/74* (2016.02); *B25J 9/163* (2013.01); *B25J 9/1633* (2013.01); *A61B 2034/2055* (2016.02); *A61B 2034/2059* (2016.02); *A61B 2034/2065* (2016.02); *A61B 2034/302* (2016.02); *A61B 2090/064* (2016.02); *A61B 2090/3937* (2016.02); *A61B 2090/3941* (2016.02)

(58) Field of Classification Search
CPC ........ A61B 2034/302; A61B 2090/064; A61B 2034/2059; A61B 2090/3937; A61B 2034/2065; A61B 2034/2055; A61B 2090/3941
See application file for complete search history.

(56) References Cited

U.S. PATENT DOCUMENTS

| | | | |
|---|---|---|---|
| 7,892,243 | B2 | 2/2011 | Stuart |
| 8,073,528 | B2 | 12/2011 | Zhao et al. |
| 8,918,211 | B2 | 12/2014 | Diolaiti et al. |
| 9,220,570 | B2 | 12/2015 | Kim et al. |
| 2004/0243147 | A1 | 12/2004 | Lipow |
| 2008/0292194 | A1 | 11/2008 | Schmidt |
| 2011/0015649 | A1* | 1/2011 | Anvari .................. A61B 34/20 606/130 |
| 2011/0306985 | A1 | 12/2011 | Inoue et al. |
| 2013/0274596 | A1 | 10/2013 | Azizian et al. |
| 2013/0338479 | A1 | 12/2013 | Pogue et al. |
| 2014/0094968 | A1 | 4/2014 | Taylor et al. |
| 2014/0184608 | A1 | 7/2014 | Robb et al. |
| 2014/0222023 | A1 | 8/2014 | Kim et al. |
| 2015/0094736 | A1 | 4/2015 | Malackowski et al. |
| 2015/0213652 | A1 | 7/2015 | Voigt et al. |
| 2015/0235360 | A1 | 8/2015 | Zheng et al. |
| 2016/0135729 | A1 | 5/2016 | Mestha et al. |

OTHER PUBLICATIONS

Partial International Search and Written Opinion dated Nov. 30, 2017, for International Application No. PCT/US2017/048067, filed Aug. 22, 2017, 16 pages.

International Search Report and Written Opinion from the International Searching Authority dated Feb. 6, 2018, for International Application No. PCT/US2017/048067, filed Aug. 22, 2017, 21 pages.

Krupa et al., "Autonomous retrieval and positioning of surgical instruments in robotized laparoscopic surgery using visual servoing and laser pointers," Strasbourg I University, Louis Pasteur—LSIIT (UMR CNRS 7005), pp. 1-6.

Schulman et al., "A Case Study of Trajectory Transfer Through Non-Rigid Registration for a Simplified Suturing Scenario," Department of Electrical Engineering and Computer Sciences, University of California at Berkeley, CA, pp. 1-7.

Straub et al., "Autonomous High Precision Positioning of Surgical Instruments in Robot-Assisted Minimally Invasive Surgery under Visual Guidance," Mar. 2010, pp. 64-69, DOI: 10.1109/ICAS.2010.18.

Notice of Reasons for Rejection, dated Feb. 18, 2020, issued in related Japanese Patent Application No. 2019-506135, filed Aug. 22, 2017, 9 pages.

* cited by examiner

US 11,026,754 B2

MOTION EXECUTION OF A ROBOTIC SYSTEM

REFERENCE TO RELATED APPLICATIONS

This application is a continuation of U.S. patent application Ser. No. 15/675,029, filed Aug. 11, 2017, which claims the benefit of U.S. Provisional Application No. 62/379,445, filed Aug. 25, 2016, the entire contents of which are incorporated by reference herein for all purposes.

TECHNICAL FIELD

The present disclosure relates generally to tracking and correcting motion of a robotic system.

BACKGROUND INFORMATION

In robotics where motion is controlled by humans, the intended robotic motion is rarely executed perfectly because of mechanical imperfections of the robotic system, variable payloads, and contact forces. For automatic systems, payload has to be taken into consideration in motion planning, otherwise there may be mismatch between the desired and actual motion. In surgical robotics, lack of compliance may be a challenge in systems that aim to perform automatic surgery. Lack of compliance may also be an issue, however, for master/slave systems. With such systems, a surgeon may learn to compensate for these imperfections in his/her head, and an experienced surgeon does so unconsciously. For a novice surgeon, however, the system may be non-intuitive, and he/she has to continuously adjust or correct the trajectories. Inaccurate positioning is part of what makes surgical robotics challenging to perform. If a tool would move precisely as expected, learning surgical robotics would be easier, which would translate into better clinical outcomes for all the patients.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for motion execution with a robotic system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The instant disclosure provides systems and methods for enhanced motion execution with a surgical robot. More specifically, these systems and methods may be used to correct the motion of a surgical instrument. A machine learning algorithm may be trained by collecting data relating to movement of a surgical instrument (e.g., a scalpel, punch biopsy equipment, etc.) coupled to, and controlled by, a surgical robot. Subsequently, the machine learning algorithm may adjust the movement of the surgical instrument to better account for the relative toughness of tissues in the human body. For example, if the surgical instrument encounters a tough muscle, it is likely that more force will be required to move the surgical instrument through the muscle (relative to other tissue). The machine learning algorithm may then instruct the surgical robot to apply this additional force to ensure smooth and accurate cutting of the muscle.

Figure 1:
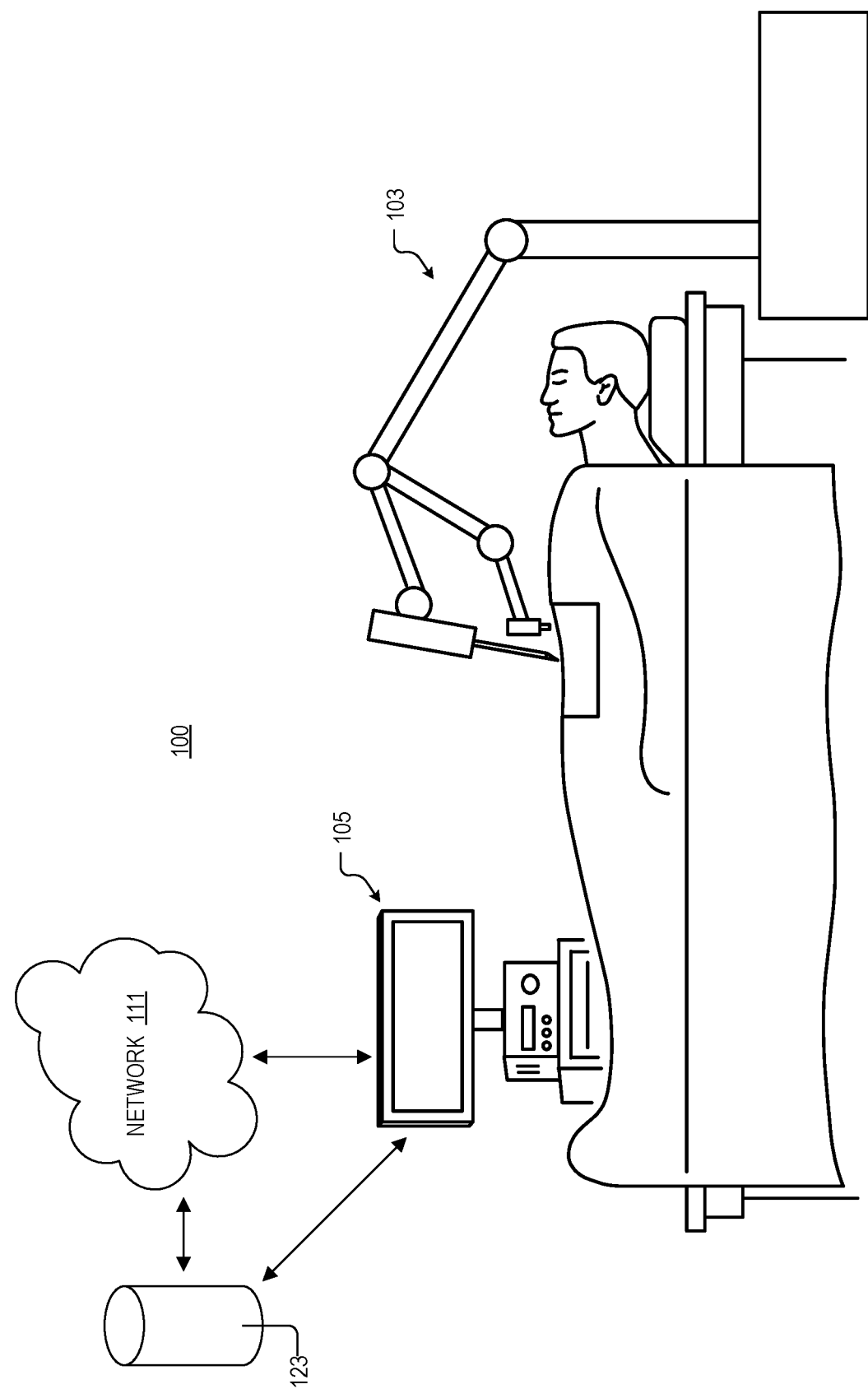
FIG. 1 illustrates a system for robotic surgery, in accordance with an embodiment of the disclosure.

FIG. 1 illustrates system 100 for robotic surgery, in accordance with an embodiment of the disclosure. System 100 includes surgical robot 103, processing apparatus 105, network 111, and storage 123. As shown, surgical robot 103 may be used to hold surgical instruments (e.g., on the distal ends of arms) and perform surgery, diagnose disease, take biopsies, or conduct any other procedure a doctor could perform. While the surgical robot 103 depicted only has two arms, one skilled in the art will appreciate that surgical robot 103 is merely a cartoon illustration, and that surgical robot 103 can take any number of shapes depending on the type of surgery needed to be performed and other requirements. Surgical robot 103 may be coupled to processing apparatus 105, network 111, and/or storage 123 either by wires or wirelessly. Furthermore, surgical robot 103 may be coupled (wirelessly or by wires) to a user input/controller (e.g., to controller 201 depicted in FIG. 2A) to receive instructions from a surgeon or doctor. The controller, and user of the controller, may be located very close to the surgical robot 103 and patient (e.g., in the same room) or may be located many miles apart. Thus surgical robot 103 may be used to perform surgery where a specialist is many miles away from the patient, and instructions from the surgeon are sent over the internet or secure network (e.g., network 111). Alternatively, the surgeon may be local and may simply prefer using surgical robot 103 because it can better access a portion of the body than the hand of the surgeon.

In one embodiment, image/optical sensors, pressure sensors (stress, strain, etc.) and the like are all used to control surgical robot 103 and ensure accurate motions and applications of pressure. Furthermore, these sensors may provide information to a processor (in surgical robot 103, processing apparatus 105, or other device) which uses a feedback loop to continually adjust the location, force, etc. applied by surgical robot 103.

In one embodiment, surgical robot 103 can be used for data collection, and the data collected can be used to further improved the algorithms controlling surgical robot 103. For instance, surgical robot 103 may attempt to move a surgical instrument through a medium (e.g., human tissue) to a desired position. For example, surgical robot 103 may try to cut through a piece of skin by moving a scalpel 3.1 cm to the left. During or after cutting, the actual position of the surgical instrument is measured. Subsequently, the difference between the actual position and the desired position of the instrument may be calculated and recorded. For example, surgical robot 103 may have moved the scalpel only 2.9 cm to the left because a portion of the skin it was cutting through is callused—requiring more force to move the scalpel. Thus, the difference between the actual and desired position is 0.2 cm. Composition of the medium (e.g., skin with a callus) and the force needed to move the surgical instrument through the medium are recorded. In one embodiment, the composition of the medium is determined optically (e.g., an image sensor takes a picture of where the scalpel is cutting, and the image is compared to a database of images to determine that the medium is skin). The composition of the medium and the force needed to move through the medium may be stored in a database (on processing apparatus 105, on network 111, or on storage 123). All of these devices may be distributed systems.

The information in the database may be used to train a machine learning algorithm. The machine learning algorithm learns from the type of medium and force needed to move the surgical instrument, to adjust the actual position and force applied to the surgical instrument in use. This allows surgical robot 103 to proportionally respond when encountering a specific type of medium with the surgical instrument. For example, the machine learning algorithm may be trained to recognize harder tissues (thick muscle, tendons, etc.) and apply additional force when the surgical instrument (e.g., scalpel, biopsy tool, etc.) encounters these mediums. Alternatively, surgical robot 103 may be trained to apply less force when navigating soft tissue. Surgical robot 103 can recognize different types of tissue both optically (e.g., from images captured with an image sensor) and/or from tactile sensors (e.g., the amount of pressure it takes to cut the material).

In one embodiment the information collected in the database can be used to diagnose a problem with surgical robot 103, using the difference between the actual position and the desired position. The difference between the desired position and actual position may be attributed to at least one of a hardware failure in surgical robot 103 or a software failure. For example, a user of surgical robot 103 could move a surgical instrument through a known medium (e.g., air) and measure the difference between the desired and actual position. If there is a discrepancy between the desired and actual position this may be used to diagnosis an issue with surgical robot 103. For instance, the Y-axis movement of one part of the surgical instrument may only be moving a small percentage of what it should be. Accordingly, surgical robot 103 or processing apparatus 105 may instruct a technician to check a Y-actuator in that portion of surgical robot 103 for damage. Similarly, collected information might also inform system design and be taken into consideration in future generations of surgical robot 103: areas of bigger mismatch are investigated through root cause analysis and the mechanical design is adjusted accordingly to minimize mismatch between actual and desired position.

In one embodiment the actual position of surgical robot 103 is corrected during surgery. As stated, a surgical instrument may be moved through a medium using surgical robot 103, and the surgical robot 103 attempts to move the surgical instrument to a desired position. The difference between the actual position of the surgical instrument and the desired position is measured. Then, the actual position of the surgical instrument is adjusted to the desired position. This process may occur continuously (iteratively), at preset intervals, or in real time.

In one embodiment adjusting the actual position of the surgical instrument includes using a machine learning algorithm to control surgical robot 103 to compensate for discrepancies in the force needed to cut through specific biological media. In this and other embodiments, the machine learning algorithm is trained to recognize a composition of a medium (e.g., skin, muscle, tendon, etc.) and output a force sufficient to move the surgical instrument from the actual position to the desired position through the medium. For example, the machine learning algorithm may recognize that a scalpel held by surgical robot 103 is trying to cut through tendon. Accordingly, the machine learning algorithm may apply additional force to the scalpel in order to make a smooth direct cut. In one embodiment, the medium (e.g., biological tissue) is recognized by the machine learning algorithm via at least one of optical appearance, the force sufficient to move the surgical instrument through the medium, input from a user of the surgical instrument, and/or the difference between the actual and desired positions of the surgical instrument. However, in other embodiments, surgical robot 103 may output a force sufficient to move the surgical instrument through the medium without explicit recognition of the medium. In another or the same embodiment, when moving the surgical instrument to the desired position, the difference between actual and desired position could be converted into haptic feedback which is provided to the user (e.g., desired position wasn't achieved, but the user now knows it because of a controller vibration).

Figure 2A:
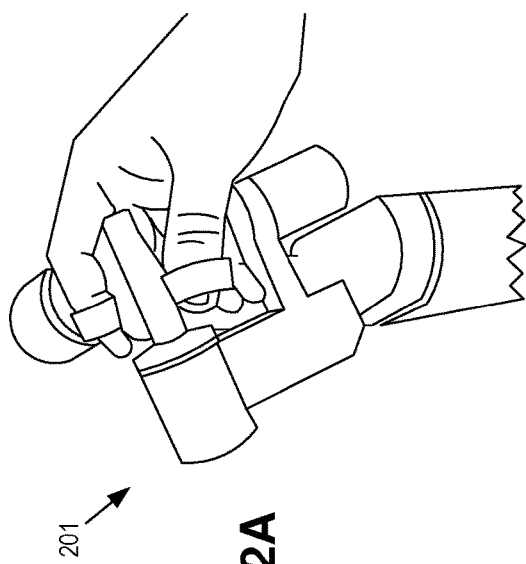
FIG. 2A illustrates a controller for robotic surgery, in accordance with an embodiment of the disclosure.

FIG. 2A illustrates a controller 201 for robotic surgery, in accordance with an embodiment of the disclosure. In the depicted embodiment, controller 201 includes several loops for the user (surgeon) to put their fingers through and grasp controller 201. Further, there are several pivot points so the user has close-to-free range of motion (similar to actually performing surgery). In one embodiment, controller 201 allows the user to feel differences between various media by changing the resistance the user encounters (e.g., haptic feedback) when performing surgery. For example, if the user moves controller 201 so that the surgical instrument attached to the surgical robot (e.g., surgical robot 103) moves through air and then moves through biological tissue, the user will feel that moving through air requires relatively minimal effort, but upon encountering biological tissue, the user will feel resistance equal or proportional to the resistance encountered by the surgical instrument. In some embodiments, the motions of controller 201 may be scaled so that the surgical instrument moves a smaller or larger distance than the user moves controller 201. In one embodiment, controller 201 may also filter out tremor or other sporadic actions from the user's movement. Although the embodiment of controller 201 depicted in FIG. 2A has several pivot points and finger loops, one skilled in the art will appreciate that there are many ways controllers can be configured to facilitate different types of surgery. In one embodiment, controller 201 may have joysticks, buttons, or the like.

Figure 2B:
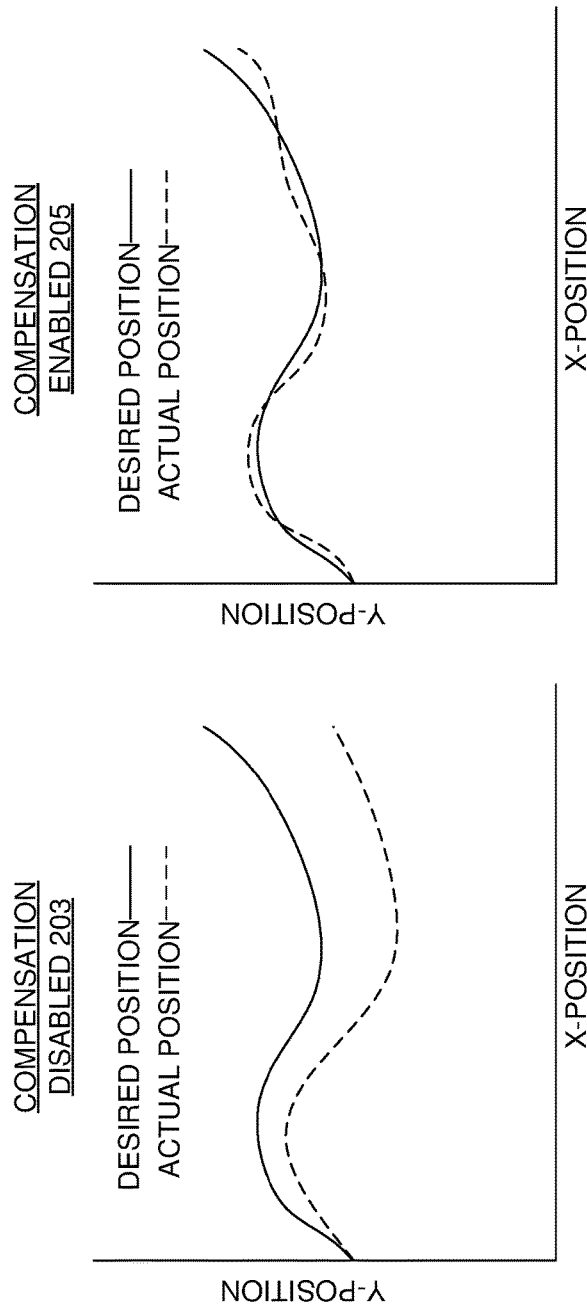
FIG. 2B shows plots illustrating compensation disabled and compensation enabled surgical instrument paths, in accordance with an embodiment of the disclosure.

FIG. 2B are plots illustrating compensation disabled 203 and compensation enabled 205 surgical instrument paths, in accordance with an embodiment of the disclosure. Both graphs only show hypothetical X and Y positions of a surgical instrument held by a surgical robot. The left-hand graph shows compensation disabled surgical robot motion. As illustrated after the surgical instrument moves a distance through a medium there is a discrepancy between the desired position of the surgical instrument and the actual position of the surgical instrument. This is problematic because even small differences in the desired and actual difference of the surgical instrument may cause serious problems to the surgical patient. Moreover, discrepancies between actual and desired position may make training surgical robotics harder: the surgeon has to learn to compensate for all of the imperfections in his/her brain.

The right-hand graph shows the compensation enabled surgical robot motion. In the depicted embodiment the actual location of the surgical instrument is adjusted continually to ensure minimal deviation from the desired location. In other embodiments adjustment may occur at discrete intervals or otherwise. In one embodiment, measuring the actual position of the surgical instrument includes at least one of optically determining the actual position with one or more image sensors, measuring a distance between preset markers and the surgical instrument, or mechanically measuring the actual position of the surgical instrument with the surgical robot. In one embodiment, visual servoing (visual position feedback) is used to update the trajectory and make it conform to the intended path as provided by the surgeon using the user input device (e.g., controller 201). For example, if the surgeon moves 2 cm to the right, visual servoing ensures that the tooltip is moving by 2 cm (or the corresponding scaled motion, e.g., 0.5 cm if a scaling factor of 4 is used) to the right, in the frame of reference of the camera. This may be achieved with a plurality of image sensor placement cuts made by the surgical robot. Multiple images may be used to construct a 3D model of the active portions of the surgical robot in real time. This may allow the surgical robot to know the exact positions of the active portions relative to the parts of the body being operated on. The surgical robot can then continuously refine the movement of the active portions of the surgical robot to be in the right places at the right time and eliminate potential error.

Figure 3:
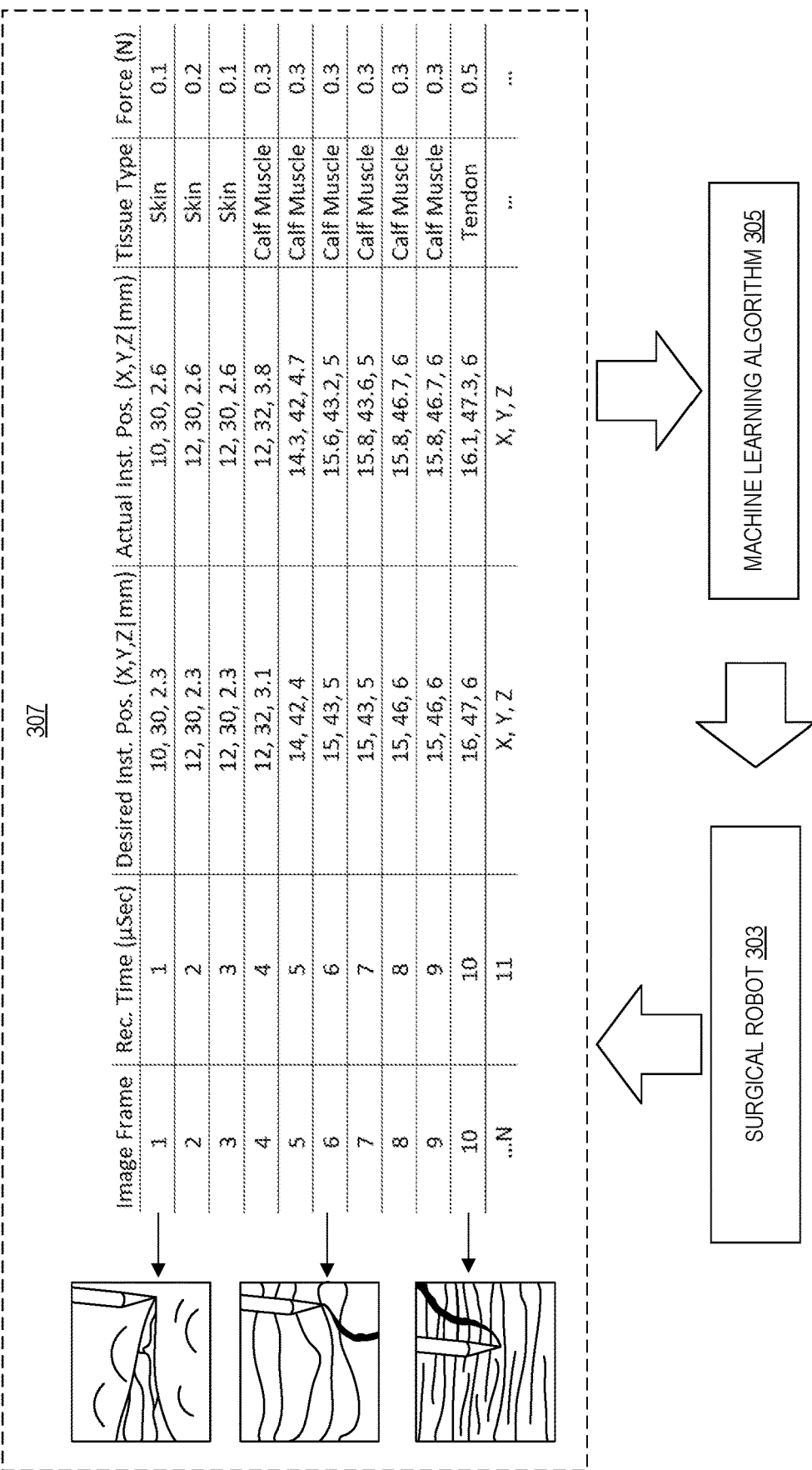
FIG. 3 illustrates a database and machine learning algorithm to be used in conjunction with robotic surgery, in accordance with an embodiment of the disclosure.

FIG. 3 illustrates a database 307 and machine learning algorithm 305 to be used in conjunction with robotic surgery (e.g., surgical robot 303), in accordance with an embodiment of the disclosure. As discussed above in connection with FIG. 1, surgical robot 303 may be used to collect information during surgery about the different biological materials encountered and the force required to cut through these materials, biopsy these materials, etc. FIG. 3 illustrates surgical robot 303 uploading this information to database 307 that includes image frames showing the tissue and the surgical instrument (these may be video or still images), the time the images were recorded (here shown as recording time), the desired position of the surgical instrument, the actual position of the surgical instrument, the tissue the surgical instrument is encountering, and the force required to cut through the tissue. As shown all of these columns in database 307 may be indexed to one another.

The information in database 307 can then be used to train machine learning algorithm 305 to help better control the actual position of surgical robot 303. This may include teaching machine learning algorithm 305 to recognize certain types of tissue either optically, by feel, or a combination of these and other parameters. Machine learning algorithm 305 may be continuously updated from one or more surgical robots (e.g., machine learning algorithm 305 may exist on the cloud and receive training data from a plurality of surgical robots around the world). Alternatively, the surgical robots and associated software could undergo periodic updates. One skilled in the art will appreciate that there are many different ways to store and update the software controlling surgical robot 303.

Figure 4:
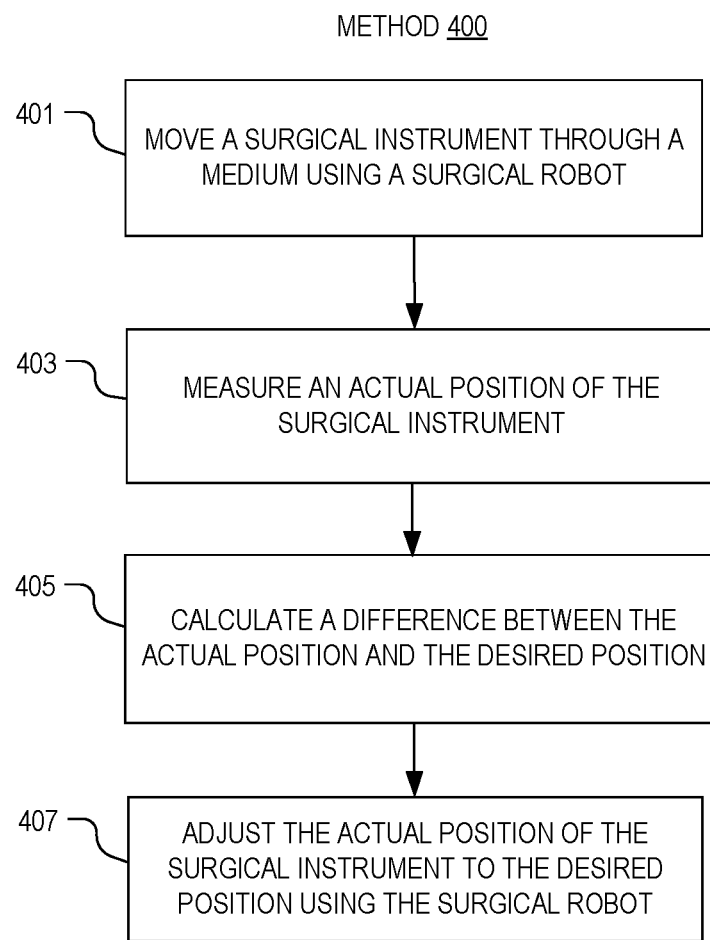
FIG. 4 illustrates a method of surgical robot operation, in accordance with several embodiments of the disclosure.

FIG. 4 illustrates a method 400 of surgical robot operation, in accordance with several embodiments of the disclosure. The order in which some or all of process blocks 401-407 appear in method 400 should not be deemed limiting. Rather, one of ordinary skill in the art having the benefit of the present disclosure will understand that method 400 may be executed in a variety of orders not illustrated, or even in parallel.

Block 401 illustrates moving a surgical instrument through a medium using a surgical robot, and the surgical robot attempts to move the surgical instrument to a desired position.

Block 403 shows measuring an actual position of the surgical instrument. This may be accomplished using image sensors included in an endoscope and the endoscope enables visual servoing, and video data coming from the endoscope is analyzed in real time. In other embodiments, the image sensors may be attached to the surgical robot itself. Instruments and instrument trajectories may also be detected using markers. For example, checkerboard patterns (quick response codes, barcodes, etc.), color dots attached to the surgical instrument, fluorescent paint/fluorescent markers may all be used alone or in conjunction with visual imaging to determine the location of the surgical instrument and moving components of the surgical robot. Labels/markers may be compatible with sterilization of the instruments/camera. Markers may also be nontoxic for insertion into the human body during surgery. Alternatively, instruments can be unlabeled, and tracking may be performed by comparing video data of the surgical instrument during surgery to a database of 3D models of the instruments. Additionally, instrument tracking may be machine learned. The video data may also be used in conjunction with the instrument data to know which instrument is being used (its 3D model can then be retrieved to help instrument detection) and what its expected position is (which reduces the space in which the instrument is searched within each video frame). In addition to this visual feedback, the expected position is collected from the surgical robot, by integrating information from the motor controller of the joints of the surgical robot. In some embodiments, position information might also be gathered by using RFID-like tags and/or magnetic sensors on the instruments. Additional information might be provided to enhance optical perception of the actual location of the surgical instrument, for example by adding a contact sensor to the tip of the instruments (e.g., with a capacitive circuit to elicit compression information derived from the distance between two plates).

Block 405 describes calculating a difference between the actual position and the desired position. This may be completed by taking the actual X, Y, Z coordinates of the surgical instrument and subtracting them from the desired X, Y, Z coordinates. The rotational information of the surgical instrument may also be accounted for. The system may then calculate the shortest distance between the sets of coordinates, or the like.

Block 407 illustrates adjusting the actual position of the surgical instrument to the desired position using the surgical robot. The system (e.g., system 100 of FIG. 1) can learn over time which trajectories and which tissue interactions require a specific amount of compensation and use that information to regularize—in a mathematical sense—the real-time compensation. It is anticipated that each surgical instrument, instrument trajectory, and tissue pattern will trigger a specific mismatch between actual and desired position. But patterns could be determined and learned by the machine learning algorithm and/or dimensionality reduction performed to reduce the space of potential adjustments. Additional constraints can be added so that real-time adjustments are always made smoothly and within safe limits (e.g., no adjustment bigger than 50% of intended move, or no adjustment bigger than 1 cm around the uncompensated position). In one embodiment, specific surgeons may select how much additional compensation the surgical robot outputs. For example, a surgeon may not be familiar with the amount of additional help the machine provides, and elect to scale back the assistance provided.

Figure 5:
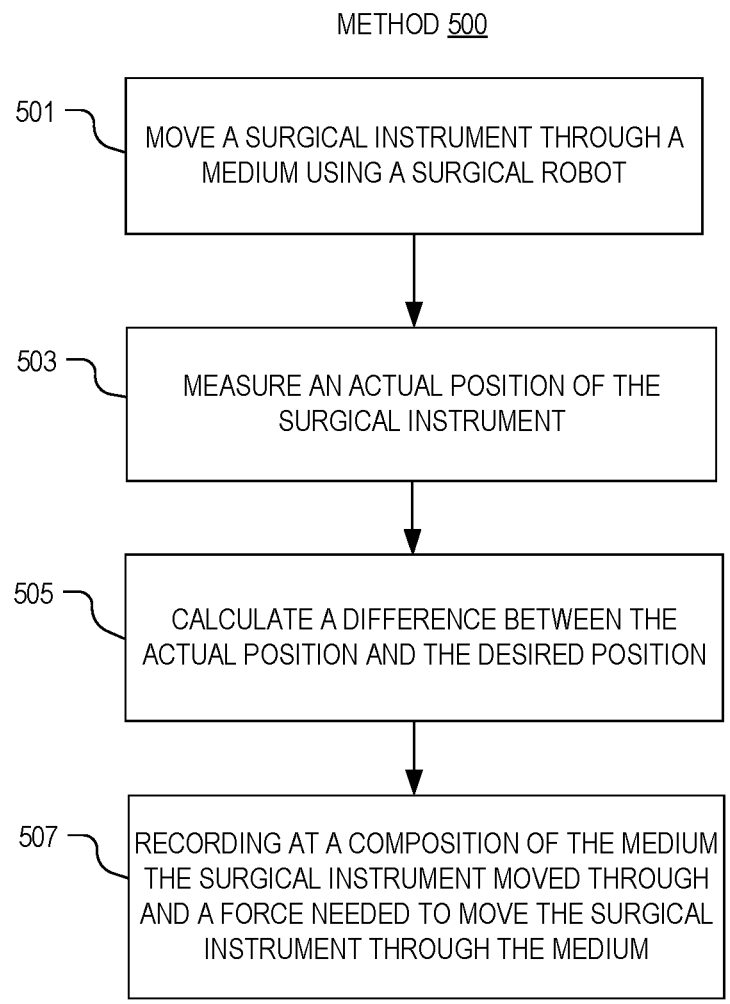
FIG. 5 illustrates a method of data collection in robotic surgery, in accordance with several embodiments of the disclosure.

FIG. 5 illustrates a method 500 of data collection in robotic surgery, in accordance with several embodiments of the disclosure. The order in which some or all of process blocks 501-507 appear in method 500 should not be deemed limiting. Rather, one of ordinary skill in the art having the benefit of the present disclosure will understand that method 500 may be executed in a variety of orders not illustrated, or even in parallel.

Block 501 illustrates moving a surgical instrument through a medium using a surgical robot, and the surgical robot attempts to move the surgical instrument to a desired position. In one embodiment the surgical instrument is permanently coupled to the surgical robot; however, in other embodiments the surgical robot may be configured to receive any number of surgical attachments that couple to one or more of its movable components.

Block 503 shows measuring an actual position of the surgical instrument. This may be accomplished via any of the ways discussed above in connection with method 400 depicted in FIG. 4, or any of the other ways discussed in connection with the other figures.

Block 505 describes calculating a difference between the actual position and the desired position. This may be accomplished via any of the ways discussed above in connection with method 400 depicted in FIG. 4, or any of the other ways discussed in connection with the other figures.

Block 507 illustrates recording at a composition of the medium the surgical instrument moved through and a force needed to move the surgical instrument through the medium. As stated above in connection with FIG. 3, recording may involve capturing this information optically, mechanically, or the like, and uploading it to a database to train a machine learning algorithm. Haptic data may also be recorded and it can be added into the model to inform the compensation algorithms. In this embodiment the system might record useful feedback information pertaining to contact forces and friction mechanisms which can further inform the machine learning algorithm.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A non-transitory machine readable storage medium storing logic, which when executed by a processing apparatus, causes the processing apparatus to perform operations including:

receiving a signal from a controller of a surgical robot;

moving, with the surgical robot and in response to the signal, a surgical instrument through a first tissue along a trajectory that passes through the first tissue and a second tissue that differs from the first tissue; and adjusting, based upon a difference between an actual position and a desired position of the surgical instrument, the actual position of the surgical instrument to the desired position by moving the surgical instrument through the second tissue using the surgical robot, wherein adjusting comprises using a machine learning algorithm to instruct the surgical robot to apply to the surgical instrument at least a force that is sufficient to move the surgical instrument through the second tissue, wherein the machine learning algorithm recognizes a composition of the second tissue based upon the force that is sufficient to move the surgical instrument through the second tissue.

2. The non-transitory machine readable storage medium of claim 1, further comprising logic which when executed causes the processing apparatus to perform operations including:

measuring the actual position of the surgical instrument; and calculating the difference between the actual position and the desired position.

3. The non-transitory machine readable storage medium of claim 1, further comprising logic which when executed causes the processing apparatus to perform operations including:

using the machine learning algorithm to recognize the composition of the second tissue using at least a resistance signal output by a sensor coupled to the surgical robot and configured to sense a resistance when moving the surgical instrument through the second tissue.

4. The non-transitory machine readable storage medium of claim 3, wherein the sensor is a pressure sensor coupled to the surgical instrument.

5. The non-transitory machine readable storage medium of claim 1, wherein moving includes instructing the surgical robot to apply an initial force that is less than the force that is sufficient to move the surgical instrument from the actual position to the desired position through the second tissue.

6. The non-transitory machine readable storage medium of claim 1, further comprising logic which when executed causes the processing apparatus to perform operations including:
motion scaling a movement of the surgical instrument through the second tissue, wherein motion scaling includes moving the surgical instrument less than indicated by the signal from the controller.

7. The non-transitory machine readable storage medium of claim 1, further comprising logic which when executed causes the processing apparatus to perform operations including:
filtering sporadic actions of a user of the controller from the signal prior to moving the surgical instrument through the first tissue in response to the signal.

8. The non-transitory machine readable storage medium of claim 7, wherein the sporadic actions include tremor.

9. The non-transitory machine readable storage medium of claim 7, further comprising logic which when executed causes the processing apparatus to perform operations including: outputting a haptic feedback signal to the controller.

10. The non-transitory machine readable storage medium of claim 9, wherein the haptic feedback signal changes a physical resistance of the controller.

11. The non-transitory machine readable storage medium of claim 1, further comprising logic which when executed causes the processing apparatus to perform operations including:
recording the composition of the second tissue and the force needed to move the surgical instrument through the second tissue.

12. The non-transitory machine readable storage medium of claim 11, wherein recording includes recording the composition of the second tissue and the force needed to move the surgical instrument through the second tissue in a database.

13. The non-transitory machine readable storage medium of claim 1, further comprising logic which when executed causes the processing apparatus to perform operations including:
diagnosing a problem with the surgical robot using the difference between the actual position and the desired position, wherein the difference is attributed to at least one of a hardware failure in the surgical robot or a software failure.

14. The non-transitory machine readable storage medium of claim 1, further comprising logic which when executed causes the processing apparatus to perform operations including:
training the machine learning algorithm based upon the composition of the second tissue and the force needed to move the surgical instrument through the second tissue.

15. The non-transitory machine readable storage medium of claim 1, wherein training the machine learning algorithm includes using the composition of the second tissue and the force needed to move the surgical instrument through the second tissue to train the machine learning algorithm to perform at least one of:
instructing the surgical robot to apply to the surgical instrument at least the force that is sufficient to move the surgical instrument from the actual position through the second tissue,
recognizing the composition of the second tissue, or
associating the second tissue with the force that is sufficient to move the surgical instrument through the second tissue.

16. The non-transitory machine readable storage medium of claim 1, wherein training the machine learning algorithm includes using the composition of the second tissue and the force needed to move the surgical instrument through the second tissue to perform at least one of:
training the machine learning algorithm to recognize the second tissue as a harder tissue and to apply a first force when moving the surgical instrument through the harder tissue, or
training the machine learning algorithm to recognize the second tissue as a softer tissue and to apply a second force, which is less than the first force, when moving the surgical instrument through the softer tissue.

17. A surgical robot comprising the non-transitory machine readable storage medium of claim 1.

18. A non-transitory machine readable storage medium storing logic, which when executed by a processing apparatus, causes the processing apparatus to perform operations including:
receiving a signal from a controller of a surgical robot; and
moving, with the surgical robot and in response to the signal, a surgical instrument to a desired position through a first tissue and through a second tissue that differs from the first tissue,
wherein moving includes using a machine learning algorithm to instruct the surgical robot to apply to the surgical instrument at least a force that is sufficient to move the surgical instrument through the second tissue, wherein the machine learning algorithm recognizes a composition of the second tissue based upon at least the force that is sufficient to move the surgical instrument through the second tissue.

19. The non-transitory machine readable storage medium of claim 18, wherein moving includes moving an actual position of the surgical instrument to a desired position through the second tissue using the surgical robot, based upon a difference between the actual position and the desired position.

20. The non-transitory machine readable storage medium of claim 19, further comprising logic which when executed causes the processing apparatus to perform operations including:
measuring the actual position of the surgical instrument; and
calculating the difference between the actual position and the desired position.

* * * * *